United States Patent
Hontsu et al.

(10) Patent No.: US 8,454,987 B2
(45) Date of Patent: Jun. 4, 2013

(54) BIOCOMPATIBLE TRANSPARENT SHEET, METHOD FOR PRODUCING THE SAME, AND CULTURED CELL SHEET USED THE SAME SHEET

(75) Inventors: Shigeki Hontsu, Hirakata (JP); Hiroaki Nishikawa, Iwade (JP); Masanobu Kusunoki, Iwade (JP); Ryouta Hatanaka, Kishiwada (JP)

(73) Assignees: Kinki University, Osaka (JP); Japan Science and Technology, Saitama (JP)

( * ) Notice: Subject to any disclaimer, the term of this patent is extended or adjusted under 35 U.S.C. 154(b) by 966 days.

(21) Appl. No.: 12/225,256

(22) PCT Filed: Mar. 14, 2007

(86) PCT No.: PCT/JP2007/055028
§ 371 (c)(1),
(2), (4) Date: Apr. 1, 2009

(87) PCT Pub. No.: WO2007/108373
PCT Pub. Date: Sep. 27, 2007

(65) Prior Publication Data
US 2009/0311297 A1   Dec. 17, 2009

(30) Foreign Application Priority Data
Mar. 17, 2006 (JP) .................... 2006-074254

(51) Int. Cl.
*A61K 9/00* (2006.01)
*B32B 18/00* (2006.01)
*B32B 3/24* (2006.01)
*A61P 43/00* (2006.01)
*A61K 35/12* (2006.01)

(52) U.S. Cl.
USPC ........... 424/422; 428/220; 428/131; 427/596; 427/294; 427/248.1; 427/372.2; 427/377; 424/93.7

(58) Field of Classification Search
None
See application file for complete search history.

(56) References Cited

U.S. PATENT DOCUMENTS

| | | | | |
|---|---|---|---|---|
| 4,932,973 A | * | 6/1990 | Gendler | 623/23.63 |
| 5,242,706 A | * | 9/1993 | Cotell et al. | 427/2.27 |
| 6,268,695 B1 | | 7/2001 | Affinito | |

FOREIGN PATENT DOCUMENTS

| | | |
|---|---|---|
| JP | 7-88819 | 4/1995 |
| JP | 10-156814 | 6/1998 |
| JP | 10-287411 | 10/1998 |
| JP | 2001-157574 | 6/2001 |
| JP | 2004-26963 | 1/2004 |
| JP | 2004-209261 | 7/2004 |
| JP | 2005-608 | 1/2005 |
| JP | 2005-278609 | * 10/2005 |

OTHER PUBLICATIONS

Oyane, A. et. al, Chemistry Letters, 2006, v. 35, No. 11, 1300-1301.*
Hontsu, S.; et. al, Jpn. J. Applied Physics, 1996, v. 35, 1208-1210.*
Windeler, A. S.; Hestilow, K. L., J. of Tissue Culture, 1994, 16, 173-175.*
Xu, G.; et. al, J. Am. Chem. Soc., 2001, 123, 2196-2203.*
English Translation of JP2005-278609, Oct. 2005.*
International Search Report issued Apr. 17, 2007 in the International (PCT) Application of which the present application is the U.S. National Stage.
Ozeki et al., "Phase composition of sputtered films from a hydroxyapatite target", *Surface & Coatings Technology*, vol. 160, No. 1, pp. 54-61, 2002.
Hatanaka et al., "Laser Ablation Method ni yori Sakusei shita Seitai Apatite Hakumaku no Kotsuga Saibo Baiyo ni yoru Seitai Shinwasei no In Vitro Hyoka", The Annual Meeting of the Japanese Society for Biomaterials Yokoshu, 2005, p. 110.
Ogawa et al., "Kisokuteki ni Keijo Seigyo sareta Hydroxyapatite Hakumaku Hyomen no Saibo Baiyo Ashiba eno Riyo", The Annual Meeting of Japanese Society for Biomaterials Yokoshu, 2005, p. 201.
Hatanaka et al., "Hydroxyapatite Tomei Sheet no Sakusei", 2006 Nen (Heisei 18 Nen) Shunki Dai 53 Kai Oyo Butsurigaku Kankei Rengo Koenkai Koen Yokoshu Separate vol. 1 (2006 Nen 3 Gatsu 22 Nichi Hakko) p. 251.
Hatanaka et al., "Tomei Apatite Sheet-jo deno Seisaibo Kansatsu", 2006 Nen (Heisei 18 Nen) Shuki 67 Kai Extended abstracts; the Japan Society of Applied Physics Separate vol. 3 (2006 Nen 8 Gatsu 29 Nichi Hakko) p. 1176.

* cited by examiner

*Primary Examiner* — Mina Haghighatian
*Assistant Examiner* — Erin Hirt
(74) *Attorney, Agent, or Firm* — Wenderoth, Lind & Ponack, L.L.P.

(57) ABSTRACT

The present invention provides a flexible, biocompatible transparent sheet (8) which has high biocompatibility and a high ability to adsorb a biologically relevant substance, which can be used as a novel biomaterial, and which can be used to observe the propagation, differentiation, and/or the like of living cells in real time. The biocompatible transparent sheet (8) is produced in such a manner that a biocompatible ceramic film (2) is formed on a substrate (1) soluble in a solvent (11) incapable of dissolving biocompatible ceramics by using exemplary a laser ablation process, the substrate (1) depositing the film (2) is dipped in the solvent (11) and dissolved off, and the isolated film (2) is then dried. The biocompatible transparent sheet (8) is utilizable of producing a flexible cultured cell sheet which can be directly transplanted to an affected area. The cell sheet can be prepared in such a manner that cells are seeded on the biocompatible transparent sheet (8) and then propagated.

17 Claims, 9 Drawing Sheets

Fig. 9

BIOCOMPATIBLE TRANSPARENT SHEET, METHOD FOR PRODUCING THE SAME, AND CULTURED CELL SHEET USED THE SAME SHEET

TECHNICAL FIELD

The present invention relates to a biocompatible transparent sheet which exhibits a biocompatibility and a high bioadherence of ability to adsorb a biologically relevant substance, which can be used as a novel biomaterial, and which can be used to observe the propagation, differentiation, and/or the like of living cells in real time; a method for producing the biocompatible transparent sheet; and a cell sheet which is prepared in such a manner that cells are seeded on the biocompatible transparent sheet and then propagated.

BACKGROUND ART

Biocompatible ceramics such as hydroxyapatite have high biocompatibility; hence, metals and ceramics coated with hydroxyapatite are excellent biomaterials. It has been confirmed that the propagation and/or differentiation of cells can be promoted in such a manner that the cells are cultured on substrates of these materials (see Patent Document 1). Sheets coated with the biocompatible ceramics have high abilities to adsorb biologically relevant substances and therefore have been investigated for use as isolation/analysis sheets for nucleic acids, proteins, and the like (see Patent Documents 2 and 3). Furthermore, there are transparent strips which are used to directly observe living cells and which are prepared by grinding a bulk of biocompatible ceramics sintered at high temperatures.

In addition to these sheets, a high bioadherence cultured cell sheet laminated on a porous film made from a hydrophobic organic solvent solution containing a biodegradable polymer and an amphipatic polymer (see Patent Document 4) or fibrous film, and a layered sheet of such high bioadherence cultured cell sheet (see Patent Document 5) are known hitherto.

Substrates coated with biocompatible ceramics are non-flexible and therefore are limited in working range. Cells cultured on the coatings cannot be collected such that tissues composed of the cells perform desired functions. Any cell sheets that are absorbed in living organisms after transplantation cannot be prepared. Since metal and ceramic substrates are opaque, it is impossible to observe the behavior, such as adhesion or differentiation, of living cells in real time.

The biocompatible ceramic-coated sheets can adsorb the biologically relevant substances or can be used to isolate the biologically relevant substances but cannot be used to observe the interaction between the biologically relevant substances in real time because these sheets are opaque.

Further, there is a limitation on thinning the bulk of biocompatible ceramics by grinding; hence, any transparent strips which are flexible and soft cannot be obtained from the bulk biocompatible ceramics. Therefore, such transparent strips cannot be used as coating materials for tissues, such as soft tissues, required to be soft.

In addition, the porous film contains a synthetic resin of amphiphatic polymer and therefore may be biologically toxic. The high bioadherence cell culturing sheet contains the fibrin gel and therefore may cause viral infections.

Patent Document 1: Laid Open Japanese Patent Application Publication (Unexamined) No. 278609/2005
Patent Document 2: Laid Open Japanese Patent Application Publication (Unexamined) No. 88819/1995
Patent Document 3: Laid Open Japanese Patent Application Publication (Unexamined) No. 156814/1998
Patent Document 4: Laid Open Japanese Patent Application Publication (Unexamined) No. 157574/2001
Patent Document 5: Laid Open Japanese Patent Application Publication (Unexamined No. 00608/2005

SUMMARY OF THE INVENTION

It is an object of the present invention to provide a biocompatible transparent sheet that is flexible, soft, and safe. The biocompatible transparent sheet has high biocompatibility and a high ability to adsorb a biologically relevant substance, can be used as a novel biomaterial, and can be used to observe the propagation, differentiation, and/or the like of living cells in real time.

The present invention is characterized in that the biocompatible transparent sheet is produced in such a manner that a biocompatible ceramic film is formed on a substrate soluble in a solvent incapable of dissolving biocompatible ceramics and the substrate is then dissolved in the solvent.

The biocompatible transparent sheet of the present invention has much biocompatibility, a high bioadherence and a safety. Therefore, the biocompatible transparent sheet can be used as a novel biomaterial or used as a sheet for isolating or adsorbing a protein or DNA or a substrate for culturing cells. The cells cultured on such biocompatible transparent sheet can be directly used for transplantation without requiring a peeling operation or the like. The biocompatible sheet is transparent and therefore it can be used to monitor the propagation and/or differentiation of cells or biomolecular attraction in real time. The shape of the sheet can be varied by varying the shape of the substrate. The biocompatible transparent sheet is flexible and soft and therefore can be used as a coating material applied to a portion that has not been coated with the biocompatible ceramic film. If cells are seeded on the biocompatible transparent sheet, the cells are grafted thereto or propagated thereon. Hence, if the biocompatible transparent sheet is used as a substrate for cell culture, a cell sheet which can be directly transplanted to an affected area together with cells can be obtained.

DETAILED DESCRIPTION OF THE INVENTION

1. Biocompatible Transparent Sheet

A biocompatible transparent sheet according to the present invention includes only a biocompatible ceramic film including no support and is produced through steps schematically shown in FIGS. 1(a) to 1(e). The production of the biocompatible transparent sheet principally includes a film-forming step and a dissolving step and may further include a drying step and a heat-treating step for crystallization. These steps are described below in detail.

(1) Film-Forming Step

Figure 1:
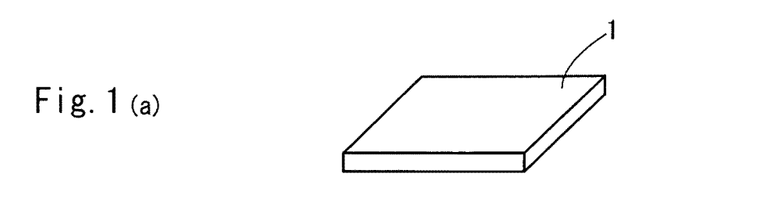
FIG. 1 shows schematic views illustrating steps of producing a biocompatible transparent sheet.

In the film-forming step, the biocompatible ceramic film 2 is formed on a substrate 1 shown in FIG. 1(a) by a laser abrasion process or the like. FIG. 1(b) shows the completion of the film.

(i) Substrate

The substrate 1 is made of a material soluble in a solvent incapable of dissolving biocompatible ceramics. The material is not particularly limited. Examples of the material include water-soluble inorganic salts, such as amorphous magnesium oxide, alkali metal halides including sodium chloride and potassium chloride, and water-soluble organic compounds such as crystalline amino acids including glycine. In particular, sodium chloride is preferable because sodium chloride can be readily crystallized and is inexpensive.

The substrate 1 has a tabular shape as shown in FIG. 1(a). The shape of the substrate 1 is not limited to such a shape. The substrate 1 may have an arbitrary shape, such as a hemispherical shape or a tubular shape, suitable for producing the biocompatible transparent sheet.

(ii) Biocompatible Ceramics

Biocompatible ceramics refer to apatite, raw materials therefore, and mixtures containing the raw materials. The appetites herein refer to minerals having the formula $M_{10}(ZO_n)_6X_2$, wherein M represents, for example, Ca, Na, Mg, Ba, K, Zn, or Al; $ZO_n$ represents, for example, $PO_4$, $SO_4$, or $CO_3$; and X represents, for example, OH, F, O, or $CO_3$. Examples of the apatite usually include hydroxyapatite and carboxyapatite. In particular, a hydroxyapatite is preferably used herein due to exhibiting a high biocompatibility. An exemplary source material of the apatite is tricalcium phosphate (TCP). An exemplary mixture containing the apatite is a bioapatite obtained from a bovine bone or the like.

(iii) Laser Abrasion Process

The laser abrasion process is explained below in reference to FIG. 2, which shows a schematic view of a laser ablation system 5.

Figure 2:
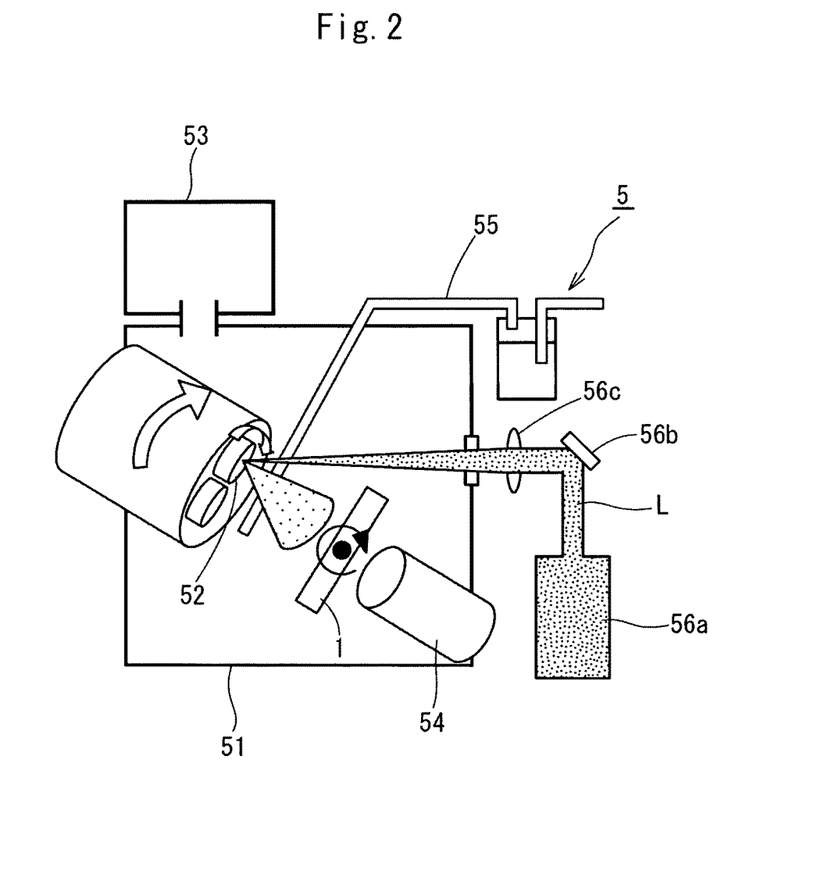
FIG. 2 is a schematic view of a laser ablation system used to produce a biocompatible transparent sheet.

As shown in FIG. 2, the substrate 1 is rotatably fixed on a sample holder (not shown) mounted in a vacuum deposition chamber 51. A molded material formed of a powder of the biocompatible ceramics by pressure forming with a pressure mold is mounted on a target 52 in a position opposed to the substrate 1.

The vacuum deposition chamber 51 is evacuated to a predetermined vacuum level with an evacuation unit 53. After having completed of evacuation, the substrate 1 is heated to a predetermined temperature with a heater 54 and rotated with the sample holder.

A steam-containing gas or a carbon dioxide-containing gas is introduced into the vacuum deposition chamber 51 through a gas introduction nozzle 55. The target 52 is irradiated with a laser beam L generated from a laser beam apparatus 56 including a laser beam generator 56, for example, a ArF excimer laser beam generator, a mirror 56b, a lens 56, and the like. This causes the biocompatible ceramics contained in the target 52 to be decomposed into atoms, ions, clusters, and/or the like, whereby a surface of the substrate 1 that faces the target 52 is covered with a biocompatible coating of apatite ceramics. Examples of the steam-containing gas include steam, an oxygen-steam mixed gas, an argon-steam mixed gas, a helium-steam mixed gas, a nitrogen-steam mixed gas, and an air-steam mixed gas. Examples of the carbon dioxide-containing gas include carbon dioxide, an oxygen-steam-carbon dioxide mixed gas, an argon-steam-carbon dioxide mixed gas, a helium-steam-carbon dioxide mixed gas, a nitrogen-steam-carbon dioxide mixed gas, and an air-steam-carbon dioxide mixed gas. These gases can be used alone or in combination.

In order to allow the biocompatible transparent sheet to be flexible and soft and in order to allow the biocompatible transparent sheet to have a predetermined strength, the biocompatible transparent sheet has a thickness of 1 to 100 μm and preferably 4 to 50 μm. Therefore, conditions for forming the biocompatible ceramic film by the laser ablation process, for example, the temperature of the substrate and the pressure of an atmosphere gas, need to be adjusted in consideration of the configuration and/or performance of the laser ablation system such that the biocompatible transparent sheet has a thickness within the above range.

(2) Dissolving Step

In the dissolving step, the substrate 1 having the biocompatible ceramic film thereon is dipped in a solvent, whereby the substrate is dissolved off. FIG. 1(c) shows a situation in which the substrate 1 having the biocompatible ceramic film 2 thereon is dipped in the solvent 11 contained in a vessel 10. FIG. 1(d) shows a situation in which the substrate 1 is dissolved off.

(i) Solvent

The solvent is not particularly limited except that the solvent is incapable of dissolving the biocompatible ceramic film 2. Examples of the solvent include polar solvents and nonpolar solvents. Preferable examples of the solvent include aqueous solvents, which are inexpensive and non-toxic. Particularly preferable examples of the solvent include pure water, buffer solutions for cell culture, and liquid culture media for cell culture.

(3) Drying Step

In the drying step, the biocompatible ceramic film 2, which is separated from the substrate 1 because the substrate 1 is dissolved off, is taken out of the solvent 11 and then naturally or mechanically dried. FIG. 1(e) shows the biocompatible ceramic film 2 that has been dried up.

As described above, the biocompatible transparent sheet can be produced by a combination of the above established techniques, that is, film formation, solvent immersion, and film drying. The above-mentioned transparent sheet having a high biocompatibility, can be used as a novel biomaterial, and can be used to observe the propagation, differentiation, and/or the like of living cells in real time.

The present invention is not limited to the above embodiment. Various modifications may be made within the scope of the present invention as set forth in the claims.

Figure 3:
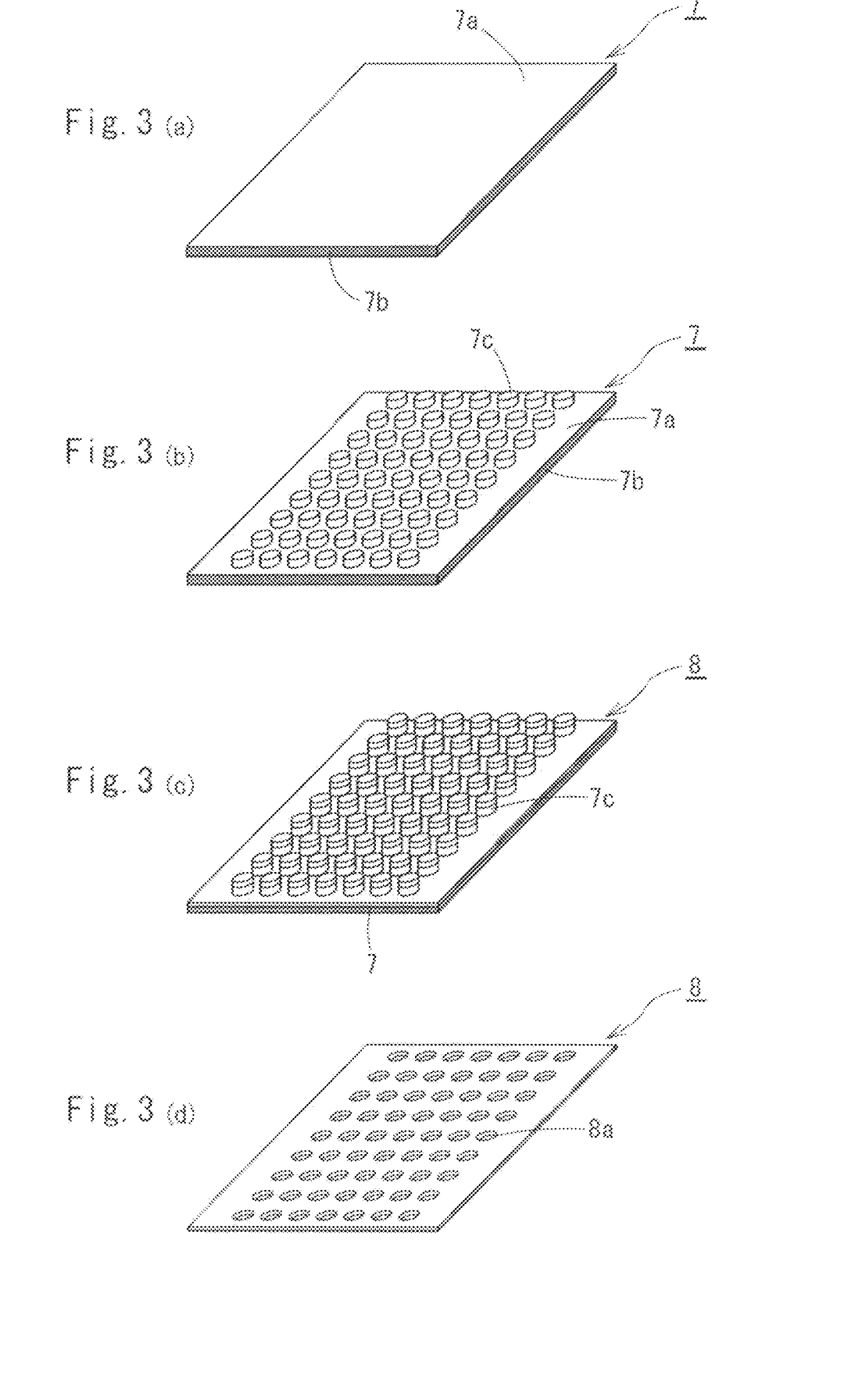
FIG. 3 shows schematic views illustrating steps of producing another biocompatible transparent sheet.

For example, a substrate 7 shown in FIG. 3(a) may be used. This substrate 7, as well as that substrate 1, includes a part 7a made of a material soluble in the solvent 11 and another part 7b made of a material, such as glass or steel, insoluble in the solvent 11. As shown in FIG. 3(b), this substrate 7 may further include projections 7c which are made of a material soluble in the solvent 11 and which are arranged on the upper surface of the part 7a in a predetermined pattern.

If this substrate 7 is used, other substrates need not be prepared for the production of biocompatible transparent sheets; hence, the biocompatible transparent sheets can be produced at low cost. If this substrate 7, which includes the projections 7c arranged in a predetermined pattern as shown in FIG. 3(b), is used, a biocompatible transparent ceramic sheet 8 having perforations 8a as shown in FIG. 3(d) can be produced in such a manner that a biocompatible ceramic film 8 is formed (a film-forming step, the state of the formed film is shown in FIG. 3(c)), this substrate 7 is dissolved off (a dissolving step), and the biocompatible ceramic film 8 is then dried (a drying step) as described in the above embodiment.

This substrate 7 can be produced in such a manner that a coating of a material soluble in the solvent 11 is formed on a glass or steel sheet insoluble in the solvent 11 by a laser ablation process, a sputtering process, an ion beam deposition process, an electron beam deposition process, a vacuum evaporation process, a molecular beam epitaxy process, a chemical vapor deposition process, or the like; a liquid containing the material soluble in the solvent 11 is sprayed on the coating, and the coating is then dried.

For this biocompatible transparent sheet 8, the diameter of the perforations 8a and the distance between the perforations 8a can be controlled by varying the size of the projections 7c and the distance between the projections 7c, respectively. This is effective in controlling the rate of cell proliferation. Cells can be propagated in such a manner that substances are exchanged through the perforations 8a; hence, different types of cells can be propagated on both surfaces of this biocompatible transparent sheet 8. A multilayer sheet which contains different types of cells and which has a complicated structure can be readily produced by tacking a plurality of sheets identical to this biocompatible transparent sheet 8 having the different cells propagated on both surfaces thereof.

In the film-forming step, the following process may be used instead of the laser ablation process: for example, a sputtering process, an ion beam deposition process, an electron beam deposition process, a vacuum evaporation process, a molecular beam epitaxy process, a chemical vapor deposition process, or the like. After the biocompatible ceramic film is formed or dried, the biocompatible ceramic film may be heat-treated in a steam-containing gas or a carbon dioxide-containing gas at a high temperature of 300° C. to 1200° C. in a heat-treating step so as to be crystallized. This allows the biocompatible transparent sheet to be denser.

Furthermore, a plurality of different biocompatible ceramics may be used in combination. In particular, for example, bioapatite and stoichiometric apatite may be used in combination. The bioapatite used herein is bioabsorbable and therefore is superior in tissue inducibility. In contrast, the stoichiometric apatite used herein remains in living organisms and therefore is superior in tissue stability. A combination of these apatites is effective in producing a sheet having a tissue inducibility and tissue stability. This sheet is transparent and therefore can be used to observe living cells with a microscope by the excellent tissue-inducible effect of the bioapatite.

2. Cell Sheet

A cell sheet according to the present invention is one prepared by propagating cells on a surface of a biocompatible transparent sheet and can be directly transplanted to an affected area.

(1) Cells

Examples of the cells include, but are not limited to, corneal epithelial cells, epidermal keratinocytes, oral mucosal cells, conjunctival epithelial cells, osteoblastic cells, nerve cells, cardiac muscle cells, fibrocytes, vascular endothelial cells, hepatic parenchymal cells, adipose cells, and stem cells capable of differentiating into these cells. These cells may be used alone or in combination. The origins of these cells need not be particularly limited. Examples of the origins thereof include human, canine, cat, rabbit, rat, pig, and sheep. In the case where the cell sheet is used to human therapy, human cells are preferably used.

(2) Culturing Process

In particular, the cells are cultured as described below. The biocompatible transparent sheet is placed into a culture vessel such as a petri dish, an appropriate cell culture solution is poured into the petri dish, a culture medium is removed, and the cell culture solution is caused to penetrate the biocompatible transparent sheet. The culture medium is replaced with fresh one several times and the biocompatible transparent sheet is then left for an appropriate time, whereby the biocompatible transparent sheet is impregnated with the cell culture solution. The cells are seeded on the biocompatible transparent sheet, the cell culture solution poured into the petri dish, and the cells are then cultured for an appropriate period under ordinary culture conditions. The cell culture solution may be replaced with fresh one as required.

The cells may be propagated on both surfaces of the biocompatible transparent sheet instead of that the cells are propagated on one surface thereof. If a biocompatible transparent sheet having perforations is used and different types of cells are propagated respectively on both surfaces thereof, only humoral factors which are produced by these cells and which are released into a culture solution are allowed to pass through the perforations pass through the perforations. This provides, for example, a cell sheet which has epithelial cells (for example, epidermal keratinocytes) propagated on one surface thereof and feeder cells propagated on the other surface.

Examples of the feeder cells used include fibrocytes, tissue stem cells, and embryo-stem cells. The feeder cells are not particularly limited and may be freely modified depending on applications thereof. The epithelial cells and the feeder cells need not isolated from one type animal. However, the epithelial cells and the feeder cells are preferably isolated from one type animal in the case where this sheet is used for transplantation. Alternatively, the epithelial cells and the feeder cells are preferably isolated from human in the case where this sheet is used for human therapy.

(3) Culture Medium

A culture medium used to culture the cells may be ordinary one and is not particularly limited. Examples of the culture medium include D-MEM, MEM, HamF12 medium, and HamF10 medium. These culture media may be supplemented with a fetal calf serum or no serum. In the case where the cell sheet is used for human therapy, the culture medium preferably contains a component which has an obvious origin or which is certified to be used as a medical drug.

(4) Transplantation Technique

The cell sheet having the cells propagated thereon is directly transplanted to an affected area alone or in combination with a plurality of stacked sheets identical to the cell sheet. The use of the stacked sheets allows a three-dimensional tissue composed of the cells to be transplanted to the affected area. A technique using, for example, a pair of tweezers is used to take the cell sheet out of the culture solution, to stack the cell sheet on the sheets, and to transplant the cell sheet to the affected area.

A technique for securing the transplanted cell sheet to a living tissue is not particularly limited and may be a known one. The cell sheet may be secured to the living tissue with sutures. Alternatively, the cell sheet may be attached to the affected area and then covered with a bandage by making use of the compatibility between the cell sheet and the living tissue.

(5) Applicable Disorders

Disorders to which the cell sheet is applicable are not particularly limited. In particular, the cell sheet having chondrocytes propagated thereon can be used to treat osteoarthritis, a cardiac muscle sheet having cardiac muscle cells propagated thereon can be used to treat ischemic heart disease, and stacked cell sheets each having epidermal cells or dermal cells propagated thereon can be used to treat burn injuries, keloids, birthmarks, and the like.

The present invention is further described in detail with reference to examples below. The claims of the present application are not limited to the examples in any sense.

Example 1

(1) Production of Biocompatible Transparent Sheet

A hydroxyapatite film is formed on a substrate of sodium chloride crystal through a laser ablation process. In particular, the sodium chloride crystal substrate of 10 mm×10 mm×2.5 mm, was fixed on a sample holder mounted in a laser ablation system (which was designed by Hontsu Laboratory of the biology-oriented science and technology school of Kinki University and was manufactured by Seinan Industries Co., Ltd.) and was then treated for 18 hours by the laser ablation process using an ArF excimer laser ($\lambda$=193 nm, a pulse width of 20 nanoseconds), whereby the hydroxyapatite film was formed. The hydroxyapatite film had a thickness of about 12 $\mu$m. The temperature of a substrate was 300° C., an atmosphere gas used was an oxygen-steam mixed gas, and the mixed gas had a pressure of 0.8 mTorr.

The sodium chloride crystal having the hydroxyapatite film formed thereon was dipped in pure water such that sodium chloride was eluted, whereby the hydroxyapatite film, which was transparent, was isolated. The isolated transparent hydroxyapatite film was cleaned with pure water, naturally dried, and then post-annealed (heat-treated) at 400° C. for ten hours in an oxygen-steam atmosphere, whereby the transparent hydroxyapatite film was crystallized into a biocompatible transparent sheet.

(2) Evaluation of Produced Biocompatible Transparent Sheet

Figure 4:
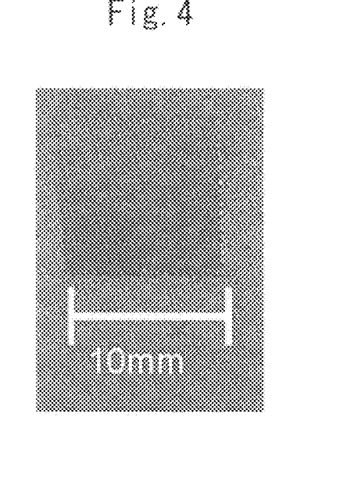
FIG. 4 is a photograph of an example of a biocompatible transparent sheet.
Figure 5:
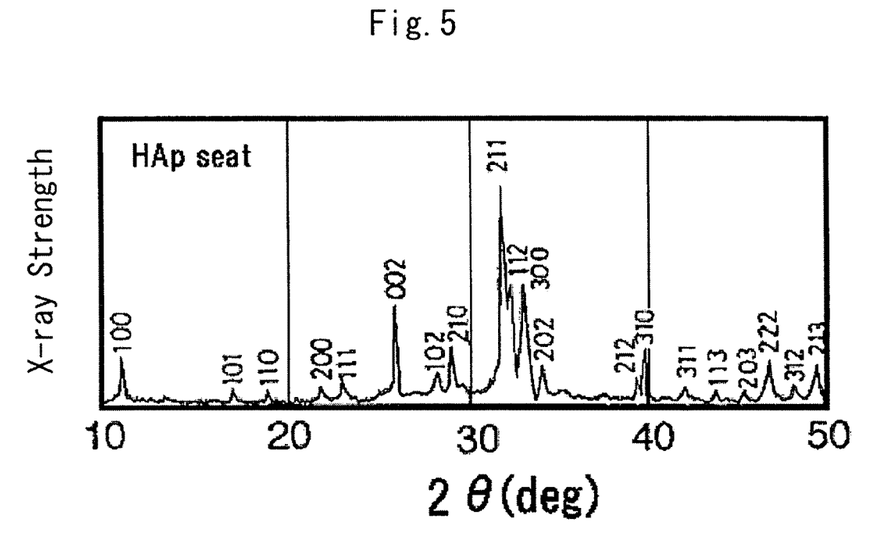
FIG. 5 is a graph showing the X-ray diffraction pattern of a biocompatible transparent sheet.
Figure 6:
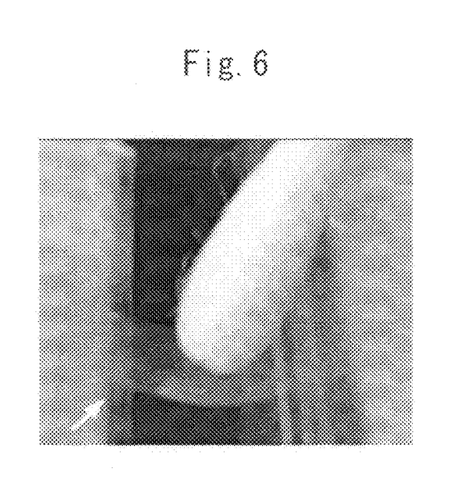
FIG. 6 is a photograph showing a situation where a biocompatible transparent sheet is forcedly bent.
Figure 7:
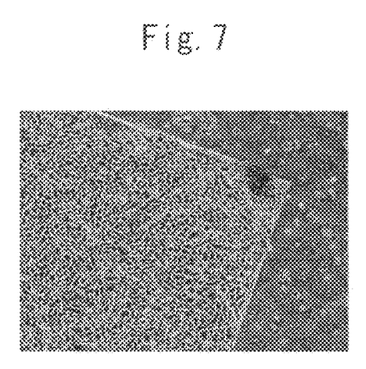
FIG. 7 is a phase-contrast micrograph of an example of a cell sheet.
Figure 8:
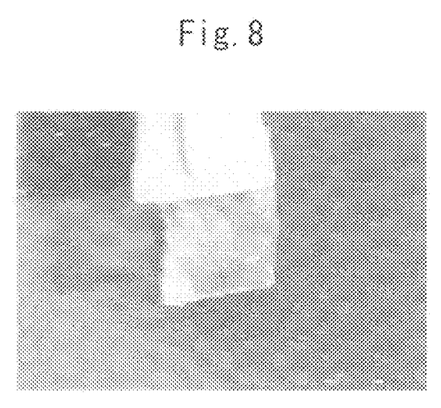
FIG. 8 is a photograph showing that a cell sheet can be grasped with a pair of tweezers.

FIG. 4 shows the biocompatible transparent sheet produced as described above. The thickness thereof was determined to be about 12 $\mu$m with a stylus-type thickness meter. The X-ray diffraction pattern of the biocompatible transparent sheet was measured by 2θ-θ X-ray diffractometry. FIG. 5 shows the measurement results. The X-ray diffraction pattern shown in FIG. 5 indicates that the biocompatible transparent sheet, which was produced by a method according to the present invention, is crystalline. A force was applied to the biocompatible transparent sheet, whereby the biocompatible transparent sheet was bent as shown in FIG. 6. This confirms that the biocompatible transparent sheet is flexible and soft. A cell sheet was prepared in such a manner that the biocompatible transparent sheet was dipped in 15% FBS-supplemented Dulbecco's modified Eagle medium (D-MEM) placed in a culture petri dish, 2 ml of a solution containing human osteoblastic cells suspended at a density of 2×10$^5$ cells/ml was poured onto the biocompatible transparent sheet, and the human osteoblastic cells were then cultured for 24 hours in an incubator (37° C., a $CO_2$ concentration of 5%). The cell sheet was observed with a phase-contrast microscope. FIG. 7 shows the observation results. After the human osteoblastic cells were cultured for 12 days, the cell sheet was capable of being grasped with a pair of tweezers as shown in FIG. 8.

Example 2

(1) Production of Biocompatible Transparent Sheet

A 2-mm thick glass plate was surface-treated for four hours by a laser ablation process in the same manner as that described in Example 1, whereby the glass plate was coated with amorphous magnesium oxide at a thickness of 5 $\mu$m. A 0.1-mm thick metal mask having holes, arranged in a matrix at intervals of 100 $\mu$m, having a diameter of 50 $\mu$m was placed onto the glass plate. The glass plate was treated for eight hours by a laser ablation process such that amorphous magnesium oxide pillars with a height of 20 $\mu$m were formed, whereby a substrate having surface micro-irregularities was prepared.

The substrate, which had the surface micro-irregularities, was fixed on a sample holder mounted in a laser ablation system and was then treated for 18 hours by a laser ablation process using an ArF excimer laser ($\lambda$=193 nm, a pulse width of 20 nanoseconds) in the same manner as that described in Example 1, whereby the substrate was coated with a hydroxyapatite film having a thickness of about 12 $\mu$m. The temperature of the substrate was equal to room temperature, an atmosphere gas used was an oxygen-steam mixed gas, and the mixed gas had a pressure of 0.8 mTorr.

Figure 9:
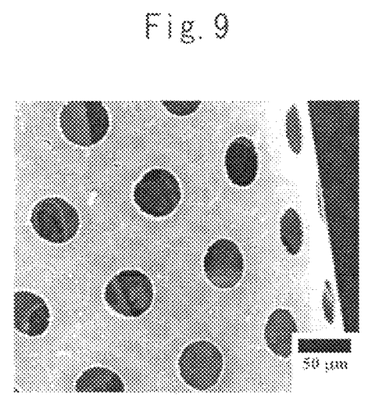
FIG. 9 is an enlarged view of another example of a biocompatible transparent sheet.

The substrate which was coated with the hydroxyapatite film was dipped in pure water such that a portion made of amorphous magnesium oxide was dissolved off, whereby the hydroxyapatite film, which was transparent, was separated from the glass plate. The separated transparent hydroxyapatite film was cleaned with pure water and then naturally dried, whereby a biocompatible transparent sheet having perforations, arranged in a matrix at intervals of 100 $\mu$m, having a diameter of 50 $\mu$m was obtained. FIG. 9 is a micrograph of the biocompatible transparent sheet.

(2) Evaluation of Produced Biocompatible Transparent Sheet

The thickness of the obtained biocompatible transparent sheet was determined to be about 12 $\mu$m with a stylus-type thickness meter.

The invention claimed is:

1. A method for producing a biocompatible transparent sheet, comprising:
    forming a biocompatible ceramic film on a substrate, the substrate being made of a water-soluble inorganic salt; and
    dissolving the substrate having the biocompatible ceramic film by dipping the substrate in a polar solvent.

2. The biocompatible transparent sheet-producing method according to claim 1, wherein the biocompatible ceramic film is formed by any one of a laser ablation process, a sputtering process, an ion beam deposition process, an electron beam deposition process, a vacuum evaporation process, a molecular beam epitaxy process, and a chemical vapor deposition process.

3. The biocompatible transparent sheet-producing method according to claim 1, further comprising:
    drying the biocompatible ceramic film after said dissolving of the substrate.

4. The biocompatible transparent sheet-producing method according to claim 1, further comprising:
    heat-treating the biocompatible ceramic film in a high-temperature atmosphere containing at least one of a steam-containing gas and a carbon dioxide-containing gas, said heat-treating being performed after said forming of the biocompatible ceramic film.

5. The biocompatible transparent sheet-producing method according to claim 1, wherein the biocompatible ceramic film is made of hydroxyapatite.

6. The biocompatible transparent sheet-producing method according to claim 1, wherein the biocompatible ceramic film comprises different types of biocompatible ceramics.

7. The biocompatible transparent sheet-producing method according to claim 3, further comprising:
heat-treating the biocompatible ceramic film in a high-temperature atmosphere containing at least one of a steam-containing gas and a carbon dioxide-containing gas, said heat-treating being performed after said forming of the biocompatible ceramic film or after said drying of the biocompatible ceramic film.

8. A method for producing a biocompatible transparent sheet, comprising:
forming a biocompatible ceramic film on a substrate, the substrate including a portion which is made of a water-soluble inorganic salt, the substrate having a projection; and
dissolving the soluble portion of the substrate having the biocompatible ceramic film by dipping the substrate in a polar solvent.

9. The biocompatible transparent sheet-producing method according to claim 8, wherein the substrate includes a portion that is insoluble in the polar solvent in addition to the polar solvent-soluble portion.

10. The biocompatible transparent sheet-producing method according to claim 1, wherein the water-soluble inorganic salt is selected from the group consisting of sodium chloride, potassium chloride, an alkali metal halide, amorphous magnesium oxide, and a combination thereof.

11. The biocompatible transparent sheet-producing method according to claim 1, wherein the polar solvent is aqueous solvent.

12. The biocompatible transparent sheet-producing method according to claim 1, wherein the polar solvent is selected from the group consisting of pure water, a buffer solution for cell culture, a liquid culture medium for cell culture, and a combination thereof.

13. The biocompatible transparent sheet-producing method according to claim 1, wherein the biocompatible transparent sheet has a thickness of 4 to 50 μm.

14. The biocompatible transparent sheet-producing method according to claim 8, wherein the water-soluble inorganic salt is selected from the group consisting of sodium chloride, potassium chloride, an alkali metal halide, amorphous magnesium oxide, and a combination thereof.

15. The biocompatible transparent sheet-producing method according to claim 8, wherein the polar solvent is aqueous solvent.

16. The biocompatible transparent sheet-producing method according to claim 8, wherein the polar solvent is selected from the group consisting of pure water, a buffer solution for cell culture, a liquid culture medium for cell culture, and a combination thereof.

17. The biocompatible transparent sheet-producing method according to claim 8, wherein the biocompatible transparent sheet has a thickness of 4 to 50 μm.

* * * * *